United States Patent [19]

Emmert

[11] Patent Number: 4,745,795

[45] Date of Patent: May 24, 1988

[54] APPARATUS FOR MEASURING GASES DISSOLVED IN WATER

[75] Inventor: Hermann Emmert, Burgbernheim, Fed. Rep. of Germany

[73] Assignee: Kraftwerk Union Aktiengesellschaft, Mülheim, Fed. Rep. of Germany

[21] Appl. No.: 18,704

[22] Filed: Feb. 25, 1987

[30] Foreign Application Priority Data

Feb. 27, 1986 [DE] Fed. Rep. of Germany ....... 3606457

[51] Int. Cl.$^4$ ............................................. G01N 31/00
[52] U.S. Cl. ...................................... 73/19; 73/61 R
[58] Field of Search ............................ 73/19, 61 R, 23

[56] References Cited

U.S. PATENT DOCUMENTS

| | | | |
|---|---|---|---|
| 3,905,222 | 9/1975 | Boillot | 73/19 |
| 4,236,404 | 12/1980 | Ketchum et al. | 73/19 |
| 4,402,211 | 9/1983 | Sugawara et al. | 73/19 |
| 4,409,814 | 10/1983 | Onuma et al. | 73/19 |
| 4,444,040 | 4/1984 | Sakai et al. | 73/19 |

FOREIGN PATENT DOCUMENTS

| | | |
|---|---|---|
| 2363370 | 6/1973 | Fed. Rep. of Germany . |
| 2632811 | 1/1978 | Fed. Rep. of Germany . |
| 3336423 | 4/1985 | Fed. Rep. of Germany . |
| 2099682 | 3/1972 | France . |
| 2235724 | 7/1973 | France . |

Primary Examiner—Stewart J. Levy
Assistant Examiner—Joseph W. Roskos
Attorney, Agent, or Firm—Herbert L. Lerner; Laurence A. Greenberg

[57] ABSTRACT

Apparatus for measuring gases dissolved in water using a gas exchanger to which the water to be tested can be supplied via a water feed line and a carrier gas can be supplied via a gas feed line, and wherein in addition to a water drainage line for degassed water, a gas drainage line for washed-out gas leads away from the gas exchanger, the gas drainage line communicating via a gas dryer with analysis and measuring instruments. The gas exchanger is a packed column disposed in an upright position, to which the water feed line and the gas drainage line are connected at the top and the gas feed line and the water drainage line are connected at the bottom. The water drainage line communicates with a collecting container. Communicating with the analysis and measuring instruments is a second branch of the gas drainage line for the gas no longer required, the second branch communicating with the collecting container. Branching off from the water drainage line is a sample line having an outlet tap for drawing off samples of water from which the gases have been removed.

12 Claims, 2 Drawing Sheets

APPARATUS FOR MEASURING GASES DISSOLVED IN WATER

BACKGROUND OF THE INVENTION

1. Field of the Invention

The invention relates to an apparatus for measuring gases dissolved in water using a gas exchanger to which the water to be tested can be supplied via a water line and a carrier gas can be supplied via a gas line, and in which leading away from the gas exchanger, besides a drainage line for degassed water, is a drainage line for washed-out gas, which communicates via a gas dryer with analysis and measuring instruments.

2. Description of the Prior Art

German patent disclosure document DE-OS No. 33 36 423 discloses an apparatus of this kind. Here argon is delivered as the carrier gas to the gas exchanger, called a contact cell; the argon then entrains the gases present in the water sample. This gas mixture is dried and then chromatically separated in a separation column. The washed-out gases are detected quantitatively by means of thermal conductivity detectors.

The known contact cell comprises a cylindrical portion in which spirally wound tubes extend. The two tubes, one of which carries the water to be tested and the other carries argon, have openings distributed uniformly over their circumference. As a result, water and argon come into contact, and the gases dissolved in the water are washed out by the argon. A gas removal line communicates with a flange on the housing, and the washed-out gas can be delivered through this gas removal line to a gas chromatograph, for example.

In a contact cell of this kind, the gas exchange is effected only up to an initially unknown equilibrium. The location of this equilibrium and hence the efficiency of the apparatus must be ascertained by calibration.

Since an apparatus for collecting the waste water and the waste gas is lacking, the known apparatus is unsuitable for monitoring contaminated water. For example, various kinds of gases are dissolved in the primary coolant of light or heavy water reactors, and for such gases it is desirable to monitor their concentration. Hydrogen and oxygen can be produced by radiolysis of water. In pressurized water reactors, the radiolysis of the primary coolant is limited. Nevertheless, the limit values of the hydrogen and oxygen concentration must be monitored. In particular, the concentration of oxygen, which is responsible for corrosion, must be monitored. The proportion of nitrogen in the primary coolant must also be monitored. Nitrogen is partly responsible for fuel element corrosion. If there is damage to the fuel elements, the noble gases krypton and xenon enter the primary coolant. An indication of the status of the fuel elements can be gained by ascertaining the concentrations of krypton and xenon.

SUMMARY OF THE INVENTION

An object of the invention is to provide an apparatus for measuring gases dissolved in water which dispenses with calibration in the liquid phase. For testing contaminated liquids, in particular the primary coolant of light and heavy water reactors, all the contaminated liquids and gases should be fed into a closed system. Also, it should be possible to draw a sample of the degassed water regardless of the pressure prevailing in the closed system.

With the foregoing and other objects in view, there is provided in accordance with the invention an apparatus for measuring gases dissolved in water, comprising, a gas exchanger wherein water to be tested is stripped of gases dissolved in the water, a water feed line connected to the gas exchanger for supplying water to be tested, a gas feed line connected to the gas exchanger for supplying a carrier gas, a water drainage line connected to the gas exchanger for discharge of degassed water from the gas exchanger, a gas drainage line connected to the gas exchanger for the release of washed-out gas from the gas exchanger, a gas dryer connected to gas drainage line for drying the gas from the gas exchanger, said gas exchanger being a packed column disposed in an upright position, to which the water feed line and the gas drainage line are connected at the top and the gas feed line and the water drainage are connected at the bottom, a collecting container connected with the water drainage line for drainage into the collecting container, a dried gas drainage line connected to the gas dryer for discharge of dried gas therefrom, analysis and measuring instruments connected to the dried gas drainage line to analyze and measure the dried gas, a second branch gas drainage line connected to the analysis and measuring instruments for passage of gas no longer required for analysis and measurement to the collecting container, and a sample line having an outlet tap branching off from the water drainage line for drawing off samples of water from which the dissolved gases have been removed.

Other features which are considered as characteristic for the invention are set forth in the appended claims.

Although the invention is illustrated and described herein as embodied in apparatus for measuring gases dissolved in water, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings in which.

DESCRIPTION OF THE PREFERRED EMBODIMENTS

Figure 1:
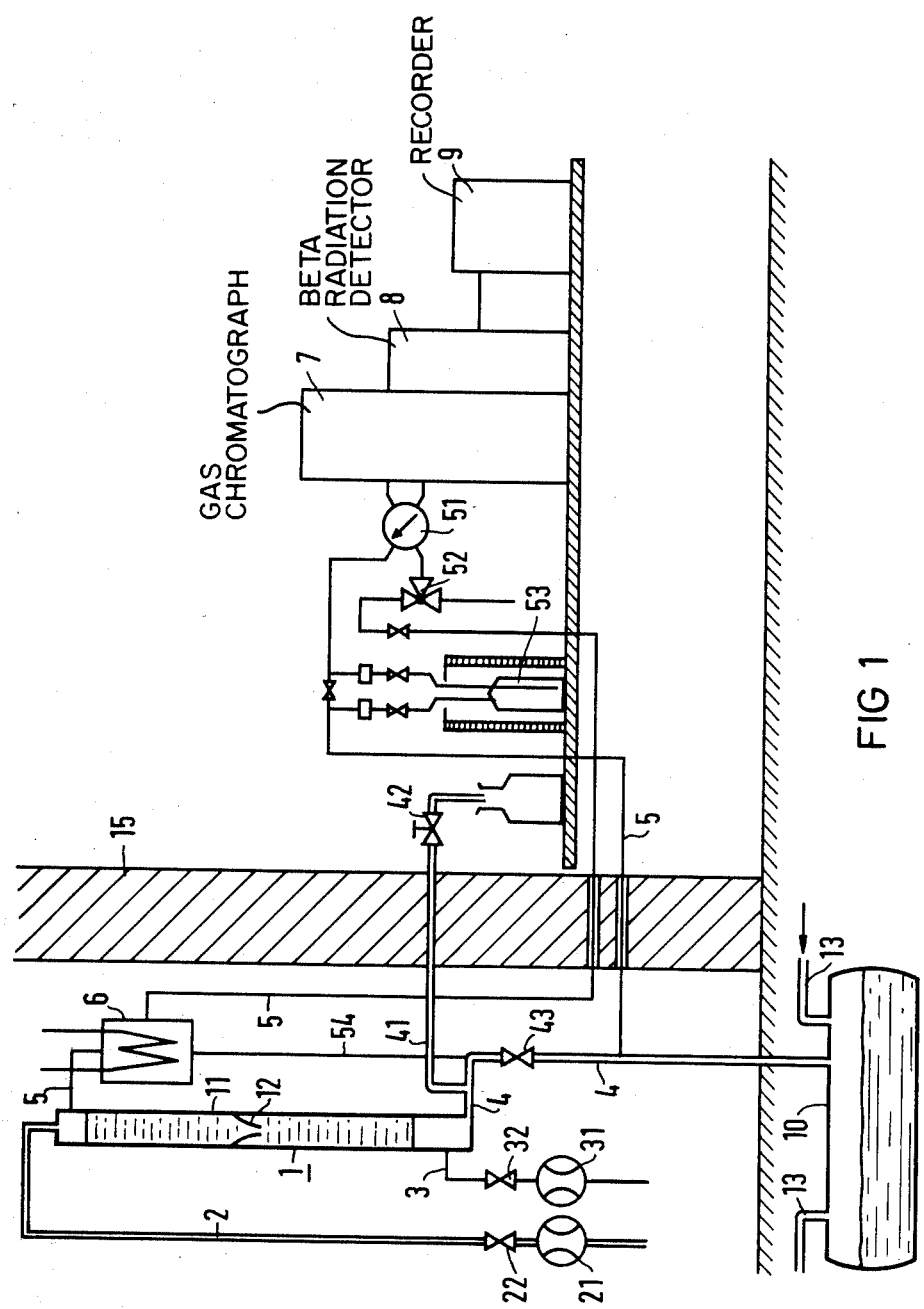
FIG. 1 diagrammatically shows apparatus according to the invention for measuring gases dissolved in water.

In accordance with the invention the gas exchanger is a packed column disposed in an upright position, to which the water feedline and the gas drainage line are connected at the top and the gas feed line and the water drainage line are connected at the bottom. The water drainage line communicates with a collecting container. A second branch of the gas drainage line for the gas no longer required communicates with the analysis and measuring instruments, and this second branch communicates with the collecting container for discharge of the gas no longer required. A sample line having an outlet tap for drawing off samples of water from which gases have been removed is disposed branching off from the water drainage line.

A packed column of this kind is virtually 100% efficient. As a result of its use according to the invention, the advantage is attained that calibrating the gas exchanger with a calibration solution, which is tedious and must be repeated frequently, is no longer necessary. It is sufficient for the analysis and measuring instruments connected following the packed column to be calibrated with test gas at regular intervals.

Test gas having a known composition is commercially obtainable and is fed into the gas drainage line, for instance via a three-way valve, upstream of the analysis and measuring instruments.

In addition to the simplicity of calibration, the advantage is attained with the apparatus in accordance with the invention that both waste water and waste gas are delivered to a collecting container, thereby preventing an uncontrolled escape of radioactive substances, when radioactive water is being tested. In a nuclear power plant, the collecting container is for instance incorporated in the internal waste gas system. Thus it receives only waste water. The waste gas is further processed in the nuclear plant.

Branching off from the water drainage line of the packed column is a sample line having an outlet tap. This enables the removal of cleaned samples of water freed of radioactive gases. Since the pressure in the collecting container is often lower than ambient pressure, however, a sample can be drawn only by using additional means. For instance, a pressure regulator is disposed in the water drainage line following the branching point of the sample line, and a bypass gas line branches off from the gas drainage line and communicates with the water drainage line directly upstream of the pressure regulator. The gas line for the tested gas communicates with the water drainage line downstream of the pressure regulator.

By the use of the pressure regulator in combination with the bypass gas line, the advantage is attained that a pressure that is greater than ambient pressure always prevails in the sample line. As a result, the outflow of the water samples when the outlet tap is opened is assured.

Problem-free outflow of the water samples from the sample line is assured in another example by embodying the water drainage line in loop form, in the fashion of a siphon. The sample line branches off from the water drainage line at the same level as the lower run of the loop. The middle leg of the siphon embodying the water drainage line is higher than a water column that generates the difference between the ambient pressure and the pressure in the collecting container. This disposition also assures that the pressure in the water drainage line is always higher than ambient pressure, which makes drawing off a sample possible at any time.

The packed column, the gas dryer, the collecting container and the lines connecting them are disposed, for instance for shielding purposes, behind an existing radiation protection wall. In that case only relatively thin feed lines and drainage lines for gas and water are extended through the radiation protection wall. This provides the advantage that when contaminated water samples, for instance from the primary loop of a nuclear power plant, are tested, the radiation exposure in the vicinity of the analysis and measuring instruments is low. These instruments can then be used and read without danger.

As the gas dryer, a gas cooler is for instance used. The condensate thereby produced is removed via a line, for instance via the bypass gas line, that communicates with the water drainage line of the packed column. As a result, the possibly contaminated condensate is also fed into the collecting container. The packed column comprises a tube that in a fixed region is filled with packing, for instance wire spirals, for increasing the surface area. The water supplied to the packing column forms a film of liquid over the entire large surface area. This promotes the exchange process between gas and liquid.

In the middle region of the tube section filled with packing, the invention provides a funnel, the wider rim of which is tightly flush with the inner wall of the tube. As a result, there is the advantage that water increasingly flowing within the peripheral region of the tube is directed back to the center of the packing section, which assures more uniform moistening of all the packing material. The funnel contributes to the high efficiency of the packed column.

Various kinds of instruments may be used as the analysis and measuring instruments. An example of an analysis instrument for the washed-out gas is a gas chromatograph, connected to a thermal conductivity detector. The components of the gas are determined thereby.

As measuring instruments for installation in the gas line for the gas to be tested, a radiation detector for detecting the radioactivity of the gases and a multichannel analyzer for nuclide-specific measurement are particularly suitable.

By way of example, a gas chromatograph having a thermal conductivity detector and a radiation detector are disposed in series. With the analysis and measuring instruments mentioned, which are known per se, required data on the gases dissolved in the water are obtained.

With the invention, the advantage is attained that the apparatus for measuring gases dissolved in water always functions reliably and is simple to calibrate. Furthermore, the apparatus according to the invention is particularly suitable for monitoring contaminated water, such as the primary coolant of nuclear power plants, because there is only minimal radiation exposure for the operating staff. All the contaminated liquids and gases can be returned to a closed system. Furthermore, the apparatus according to the invention assures that at all times water from which radioactive gases have been removed can be drawn from the system for further tests.

The measuring and analysis instruments are located outside the possible contaminated region. Instruments that are to be operated manually or automatically can be used selectively.

The invention will now be described in further detail, referring to the drawing.

The apparatus for measuring gases dissolved in water shown in FIG. 1 has as its gas exchanger a tubular packed column 1. A water feed line 2, in which a flow meter 21 and a flow regulator 22 are disposed, communicates with the upright packing container 1 at an upper connection flange. Water to be tested, which is derived for instance from the primary loop of a nuclear power plant, is supplied through the water feed line 2 at a constant volumetric flow. A gas feed line 3, in which a flow meter 31 and flow regulator 32 are disposed, communicates with the packing column 1 at a lower connection flange. Through this gas feed line 3, a carrier gas, such as argon, by which the gases dissolved in the water to be tested are washed out, is supplied at a constant volumetric flow. A water drainage line 4 for the degassed water is connected to the lower portion of the packed column 1. A gas drainage line 5 for the washed-out gas leads away from the upper portion of the packed column 1.

A predetermined tube section 11 of the packed column 1 is filled with tightly packed packing material, for instance wire spirals. The increase in surface area in the packed column 1 thereby attained improves its efficiency. To assure that all the elements of the packing are uniformly moistened by the water to be tested, a funnel 12 is disposed in the middle region of the tube section 11 filled with packing, with its wider rim tightly flush with the inner wall of the tube of the packing column 1. As a result, the water increasingly flowing in the outer region of the tube cross-section is returned to the middle once again.

The gas drainage line 5 of the packed column 1 communicates via a gas cooler 6, in which the washed-out gas is dried, with a gas chromatograph 7. Upstream of the gas chromatograph 7, a metering valve 51 and a three-way valve 52 are inserted into the gas drainage line 5 for feeding in test gas that serves to calibrate the measuring and analysis instruments.

Communicating with the gas chromatograph 7 by way of example is a beta radiation detector 8, which determines the beta activity of the gas components. For evaluation of the measurement results of the gas chromatograph 7 and beta radiation detector 8, an evaluation unit having a recorder 9 is connected to their signal outputs.

From the gas chromatograph 7 and the metering valve 51, the gas drainage line 5 continues further, and a gas sample container 53 can be connected to it.

The water drainage line 4 of the packed column 1 communicates with a collecting container 10, through which a protective gas is carried via an internal power plant line 13. Branching off from the water drainage line 4 is a sample line 41, provided with an outlet tap 42, for drawing off water samples into a sample container.

Since a slight negative pressure may prevail in the collecting container 10, additional equipment is required so that water samples can be drawn off counter to ambient pressure. As shown in FIG. 1, a pressure regulator 43 is disposed to this end in the water drainage line 4 between the branching off of the sample line 41 and the collecting container 10. Branching off from the gas drainage line 5 at the gas dryer 6 is a bypass line 54, which enters the water drainage line 4 upstream of the pressure regulator 43. As a result, a pressure that is higher than ambient pressure is assured in the sample line 41, and drawing off of a sample is always possible.

The already tested and analyzed gas which is no longer needed is fed into the collecting container 10, together with the degassed water, via the second branch of the gas drainage line 5, which communicates with the water drainage line 4 downstream of the pressure regulator 43. In the collecting container 10, the gas is flushed away with the protective gas.

Figure 2:
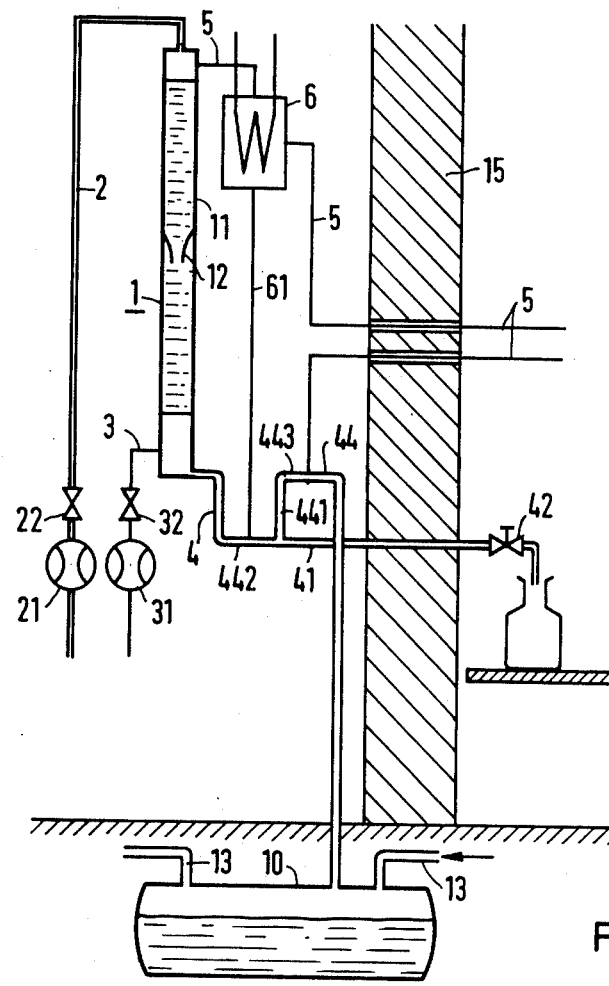
FIG. 2 is a modification of FIG. 1 and has a siphon in the water drainage line, whereas FIG. 1 has a pressure regulator in the water drainage line.

In order to assure adequately high pressure in the sample line 41, the water drainage line 4 is disposed as shown in FIG. 2 in the form of a loop, in the manner of a siphon 44. The sample line 41 branches off from the water drainage line 4 at the same level as the lower run 442 of the siphon 44. The upper run 443 of the siphon 44 is disposed high enough above the lower run 442 that the middle leg 441 of the siphon is higher then a water column the pressure of which corresponds to the difference between ambient pressure and the pressure in the collecting container 10.

The second branch of the gas drainage line 5, as shown in FIG. 2, discharges into the upper run 443 of the siphon 44. Condensate produced in the gas cooler 6 is fed via a condensate line 61 into the water drainage line 4. In the exemplary embodiment of FIG. 1, the bypass gas line 54 assumes the function of a condensate line.

In the event that radioactively contaminated water is to be tested, the apparatus according to the invention as shown in both drawing figures is arranged such that the packed column 1, the gas cooler 6, the collecting container 10 and the lines connecting them with one another are disposed behind an existing radiation protection wall 15, so as to shield them. Only thin feed lines and drainage lines for gas and water are extended through this radiation protection wall 15. The apparatus described is particularly suitable for testing primary coolant water, because in nuclear power plants the collecting container 10 and the radiation protection wall 15 are already in place. In the event that the water to be tested is inactive, however, a feed line into a collecting container 10 and a radiation protection wall 15 can be dispensed with.

What is claimed:

1. An apparatus for measuring gases dissolved in water, comprising, a gas exchanger wherein water to be tested is stripped of gases dissolved in the water, a water feed line connected to the gas exchanger for supplying water to be tested, a gas feed line connected to the gas exchanger for supplying a carrier gas, a water drainage line connected to the gas exchanger for discharge of degassed water from the gas exchanger, a gas drainage line connected to the gas exchanger for the release of washed-out gas from the gas exchanger, a gas dryer connected to gas drainage line for drying the gas from the gas exchanger, said gas exchanger being a packed column disposed in an upright position, to which the water feed line and the gas drainage line are connected at the top and the gas feed line and the water drainage are connected at the bottom, a collecting container connected with the water drainage line for drainage into the collecting container, a dried gas drainage line connected to the gas cooler for discharge of dried gas therefrom, analysis and measuring instruments connected to the dried gas drainage line to analyze and measure the dried gas, a second branch gas drainage line connected to the analysis and measuring instruments for passage of gas no longer required for analysis and measurement to the collecting container, and a sample line having an outlet tap branching off from the water drainage line for drawing off samples of water from which the dissolved gases have been removed.

2. An apparatus as defined by claim 1, wherein a pressure regulator is disposed in the water drainage line, a bypass gas line branching off from the gas drainage line communicates with the water drainage line upstream of the pressure regulator, the sample line branches off from the water drainage line upstream of the pressure regulator, and the second branch of the gas drainage line, for the no longer required gas, communicates with the water drainage line downstream of the pressure regulator.

3. An apparatus as defined by claim 2, wherein the gas dryer is a gas cooler, which communicates with the water drainage line in order to drain away condensate.

4. An apparatus as defined by claim 3, wherein the gas cooler communicates via the bypass gas line with the water drainage line, for draining away condensate.

5. An apparatus as defined by claim 1, wherein the water drainage line is disposed in loop form having a lower run, an upper run and a middle leg, after the fashion of a siphon, wherein the middle leg of the siphon is higher than a water column the pressure of which corresponds to the difference between ambient pressure and a negative pressure in the collecting container, and the sample line branches off from the water drainage line at the same level as the lower run of the siphon.

6. An apparatus as defined by claim 1, wherein the packed column, the gas dryer, the collecting container and the lines connecting them are disposed, for shielding, behind an existing radiation protection wall, and that only relatively thin feed lines and drainage lines for gas and water are extended through the radiation protection wall.

7. An apparatus as defined by claim 1, wherein the gas dryer is a gas cooler, which communicates with the water drainage line in order to drain away condensate.

8. An apparatus as defined by claim 1, wherein in the packed column in a middle region of a tube section filled with packing, a funnel is provided, the wider rim of which is tightly flush with an inner wall of the tube section.

9. An apparatus as defined by claim 1, wherein one of the analysis instruments is a gas chromatograph having a thermal conductivity detector.

10. An apparatus as defined by claim 9, wherein one of the measuring instruments is a radiation detector for measuring the radioactivity of the gases.

11. An apparatus as defined by claim 10, wherein the gas chromatograph, thermal conductivity detector and radiation detector are disposed one after another in series.

12. An apparatus as defined by claim 1, wherein one of the measuring instruments is a radiation detector for measuring the radioactivity of the gases.

* * * * *